(12) United States Patent
Gojon-Romanillos

(10) Patent No.: US 8,361,514 B2
(45) Date of Patent: Jan. 29, 2013

(54) SYSTEMIC TREATMENT OF PATHOLOGICAL CONDITIONS RESULTING FROM OXIDATIVE STRESS AND/OR REDOX IMBALANCE

(75) Inventor: Gabriel Gojon-Romanillos, San Pedro Garza Garcia (MX)

(73) Assignee: Nuevas Alternatives Naturales Thermafat, S.A.P.I. de C.V., Monterrey N.L. (MX)

( * ) Notice: Subject to any disclaimer, the term of this patent is extended or adjusted under 35 U.S.C. 154(b) by 589 days.

(21) Appl. No.: 12/543,407

(22) Filed: Aug. 18, 2009

(65) Prior Publication Data
US 2009/0304819 A1 Dec. 10, 2009

Related U.S. Application Data

(60) Continuation-in-part of application No. 12/405,165, filed on Mar. 16, 2009, which is a division of application No. 10/463,765, filed on Jun. 18, 2003, now abandoned.

(60) Provisional application No. 60/389,491, filed on Jun. 19, 2002.

(51) Int. Cl.
*A61K 9/00* (2006.01)
*A61K 33/04* (2006.01)
(52) U.S. Cl. ......... 424/706; 424/705; 424/707; 424/708
(58) Field of Classification Search .................. 424/400, 424/600, 703–712
See application file for complete search history.

(56) References Cited

U.S. PATENT DOCUMENTS

| 2,897,121 | A | | 7/1959 | Wagner |
| 4,031,267 | A | | 6/1977 | Berry et al. |
| 4,481,195 | A | | 11/1984 | Rubin |
| 4,555,522 | A | | 11/1985 | Martin |
| 4,590,183 | A | * | 5/1986 | Bailey ........................... 514/163 |
| 4,900,538 | A | | 2/1990 | Suwa et al. |
| 5,972,884 | A | * | 10/1999 | Cohen et al. .................... 424/49 |
| 6,242,491 | B1 | | 6/2001 | Kaddurah-Daouk |
| 2001/0001664 | A1 | | 5/2001 | Sherwood et al. |

OTHER PUBLICATIONS

Gojon, Gabriel, Rrelative rate constants for hydrogen atom abstraction by the cyclohexanenthiyl and benzenethiyl radicals (Author's Dissertation), Dec. 1974.
Sies, Helmut, Antioxidants in disease and therapy, Advances in Pharmacology vol. 38, Academic Press, San Diego, CA 1997.

* cited by examiner

*Primary Examiner* — Ruth Davis

(57) ABSTRACT

Alterations of redox homeostasis in mammals underlie a host of symptoms, syndromes and diseases, including AIDS and cancer, which can be successfully treated by administration to a mammal of therapeutically-effective amounts of sulfide compounds and/or thiosulfate compounds and/or thionite compounds and/or sulfite compounds and/or thionate compounds and/or any organic, inorganic or organometallic precursors thereof. The unique compositions of this invention contain one or more "active sulfur compounds" in combination with each other or with other therapeutic agents. The invention also encompasses the varying modes of administration of the therapeutic compounds. In particular, a novel method of combining active ingredient with wet cellulose is provided, which allows the wet cellulose to function as an enteric carrier.

13 Claims, No Drawings

SYSTEMIC TREATMENT OF PATHOLOGICAL CONDITIONS RESULTING FROM OXIDATIVE STRESS AND/OR REDOX IMBALANCE

CROSS-REFERENCE TO RELATED APPLICATIONS

This application is a continuation-in-part of U.S. application Ser. No. 12/405,165, filed on Mar. 16, 2009, which is a divisional of U.S. application Ser. No. 10/463,765, filed on Jun. 18, 2003, now abandoned, which claims priority to U.S. Provisional Application No. 60/389,491 filed on Jun. 19, 2002, each expressly incorporated by reference herein.

FEDERALLY SPONSORED RESEARCH STATEMENT

Not applicable.

FIELD OF THE INVENTION

The present invention relates to novel compositions for and methods of treating symptoms, syndromes, pathological conditions and disease-associated problems mediated by oxidative stress. These conditions include cancer, AIDS, diabetes, cardiovascular diseases, Down syndrome, chronic inflammatory diseases, neurodegenerative diseases, cachexia secondary to HIV-1 infection, cachexia secondary to cancer and AIDS related complex (ARC), and hypercholesterolemia. Also included is the novel preparation of active ingredient with an enteric carrier.

BACKGROUND OF THE INVENTION

The present applicant serendipitously and unexpectedly discovered a therapy system useful for treating cancer, AIDS, cardiovascular diseases, Down syndrome, chronic inflammatory diseases, diabetes, neurodegenerative diseases and other disease states mediated by oxidative stress. This system comprises the delivery to the gut of a mammal of therapeutically effective amounts of one or more of the following active agents: sulfide compounds, thiosulfate compounds, thionite compounds; sulfite compounds, thionate compounds, and any organic, inorganic or organometallic precursors thereof.

The present applicant found in a preliminary evaluative clinical trial with far-advanced human cancer patients having histologically verified malignancies representing a wide range of cancer types (breast, colon, lung, prostate, larynx, testis, uterus, pancreas, muscle lymphoma, including lymphoma in the leg or gluteal muscles, carcinoma, sarcoma) that a significant rate and extent of reduction in tumor size occurred, often followed by complete remission. The therapy system of the present invention substantially avoids several of the well-known problems and limitations of conventional cancer chemotherapy such as development of resistant malignant-cell variations, excessive concomitant toxicity, dependence on phase of cell cycle and mutagenic side effects.

In other preliminary clinical trials, the present applicant surprisingly found clear evidence of the effectiveness of essentially the same therapy system when applied to patients afflicted with Down syndrome, hypercholesterolemia and cardiovascular disease.

Although sulfur compounds have a long history of pharmaceutical usefulness, only two of the sets of compounds claimed in this application (thiosulfates and sulfites) have found wide use in pharmacology and/or in the formulation of final dosage forms as preservatives, antioxidants, or biocides. Thus, thiosulfates find application in the treatment of cyanide poisoning, allergic conditions and drug sensitization caused by gold, arsenic, mercury or bismuth preparations in humans, and in veterinary medicine as cyanide antidotes, as "general detoxifiers" and also in bloat and, externally, in treatment of ringworm or mange. Injection of aqueous solutions of sodium thiosulfate and L-cysteine or its sodium salt are claimed to be effective against "bacteria and viruses" in general. U.S. Pat. No. 4,148,885 issued to Renoux et al., discloses use of sodium thiosulfate and sodium metabisulfite as immunostimulants, but strictly within the context of "a process for stimulating the immunity of a living organism", although only mice are mentioned and only subcutaneous administration was employed.

Sulfites also display some pharmacological activity against the agents responsible for certain parasitic and infectious conditions. In addition German patent DE3419686 discloses sulfite or bisulfite solutions for treating arthritis or epilepsy. WO8402527 claims increased anti-tumor activity for adriamycin and daunomycin with the addition of sulfites, acid sulfites, pyrosulfites and/or dithionites. U.S. Pat. No. 5,045,316 issued to Kaplan, claims that a combination of an ionic vanadium compound, a thiosulfate or sulfite, and optionally selenium is useful for treating malignant tumors, atherosclerosis and mental syndromes in the elderly. However, it should be clear that in the prior art neither thiosulfates nor sulfites have been claimed to act as herein disclosed by themselves or in admixture with each other and/or with sulfide compounds, thionite compounds, or thionate compounds, when delivered to a mammal in need thereof.

It should also be appreciated that both thiosulfates and sulfites are rapidly decomposed when released in the stomach, so that oral administration of aqueous solutions, tablets, or capsules containing sulfites or thiosulfates cannot be used for their delivery to the gut of a mammal, unless an enteric coating, enteric carrier or other ad-hoc delivery system is employed. Exactly the same considerations apply to dithionites, which have been used (see above) in combination with adriamycin and daunomycin. On the other hand, sulfide compounds and thionate compounds have been, to the best of the present applicant's knowledge, neither claimed to act as herein disclosed nor hypothesized to be capable of such action when delivered to a mammal.

Without intending to be bound by any particular hypothesis or theory, current thinking on the etiology of cancer, AIDS, cardiovascular diseases, diabetes, Down syndrome, chronic inflammatory diseases and neurodegenerative disorders will be reviewed, in an attempt to understand the basis for the surprising success of the treatment method disclosed herein. Since the diverse sulfur compounds found by the present applicant to be pharmacologically active all possess reducing properties, special attention will be given to the possibility that a link exists between the two sets of properties and to research that bears on oxidation-reduction processes in cells, especially if it focuses on oxidative stress or its pathological manifestations.

In healthy human tissue a delicate balance between cell proliferation and cell death exists, which when disrupted can lead to a degenerative disease (diabetes and its vascular complications, anemia, arthritis, Parkinson's disease, Alzheimer's disease, Amyotrophic Lateral Sclerosis [ALS], Huntington's disease, muscular dystrophy, myotonic dystrophy, chronic fatigue syndrome, Friedreich's ataxia, ocular lens opacification, nephrosis, liver necrosis, dermatitis, pulmonary immune deficits, hepatic encephalopathy, macular degeneration, age-associated memory impairment, Creutzfeldt-Jacob's disease, stroke, epilepsy, peripheral neuropathy, optic neuropathy, anatomic neuropathy, neurogenic bowel disease, sensorineural deafness, neurogenic bladder dysfunction, migraine, renal tubular acidosis, dilating cardiomyopathy, hepatic failure, lactic acidemia, arsenic poisoning, silicosis, acetaminophen poisoning, asbestosis, asthma, rheumatic polyarthritis, adult respiratory distress syndrome) in case of premature cell loss. Similarly, disruption of this balance can lead to a hyperproliferative disease (cancer, AIDS, herpes simplex virus-1 infection, cytomegalovirus-induced vascular pathology, arteriosclerosis, ARC, hepatitis, trypanosomiasis, vascular restenosis, psoriasis, glomerular nephritis, transplant rejection, etc.) in case of cell over-accumulation. It must be pointed out that mitochondrial function is the key to this balance, since mitochondria regulate apoptosis—the physiological mechanism for the elimination of cells in a controlled and timely manner.

The defense mechanism of a mammal (humoral/cellular immunity mediated by non-phagocytic lymphocytes, phagocytic polymorphonuclear leucocytes, and voraciously phagocytic monocytes/macrophages) eliminates foreign bodies such as microorganisms (bacteria, rickettsias, viruses, fungi, protozoa or metazoa) and abnormal cells, including neoformed cells capable of becoming a cancerous tumor such as a carcinoma, sarcoma, myoma or lymphoid tumor through hyperproliferation.

Cancerous tumors are usually life-threatening. In humans they include, among others, prostate, colon, breast, lung, kidney, liver, lymphoma of the central nervous system (CNS), leukemia, pancreatic, gastric, esophageal, ovarian, uterine, testicular and skin tumors. Most human and animal cancer involves cells of epithelial origin, whose malignant transformation results in carcinomas, i.e., tumors of epithelial cell origin.

The balance between cell proliferation and cell death in a healthy mammal depends critically on both an intact immune system, and a finely tuned systemic balance between antioxidants and oxidants, which will be referred to hereinafter as "redox homeostasis". Moreover, redox homeostasis is also essential for the components of the immune system to function adequately.

Stepwise reduction of molecular oxygen (dioxygen) to water inside mammalian cells is the source of the ATP needed by the cell to power its multiple activities. However, the partially reduced intermediates formed during this process (superoxide radical anion, hydrogen peroxide, hydroperoxy radical and hydroxy radical) are highly reactive and their leakage can be the cause of oxygen toxicity, oxidative stress, and/or oxidative damage to biomolecules and complex cell structures such as membranes and mitochondria; these partially reduced species are known collectively as "reactive oxygen intermediates" (ROI's). Furthermore, some cells belonging to the immune system generate hypochlorous acid or ROI's ("respiratory burst") in order to use them as weapons against foreign bodies. Detoxication of xenobiotics (including drugs) is another common source of ROI's, as well as the enzymatic synthesis of prostaglandins, thromboxanes, and leukotrienes from polyunsaturated fatty acids in epithelial cells.

During the last decade, it has become evident that ROI's perform an extremely important direct role in signal transduction. Most sources of the ROI's involved in signal transduction seem to initially generate superoxide, whose disproportionation then yields hydrogen peroxide. As noted by Powis et al. ("Redox signaling and the control of cell growth and death", in Helmut Sies (ed.) "Antioxidants in disease mechanisms and therapy", Academic Press, 1997), intracellular redox signaling is the result of controlled changes in the intracellular redox state. This signaling can regulate the cell cycle, including the control of DNA synthesis, enzyme activation, and gene expression. The redox signaling operates by changing the conformation of key proteins by changing the oxidation state of cysteine residues in these proteins. These conformational changes affect the biological function of the protein. These conformationally sensitive proteins directly affect cell growth and differentiation, as well as cellular apoptosis.

A variety of experimental results, reported between 1994 and 2000, illustrate the importance of redox status/ROI's in cellular signaling systems and mammalian health. Metallothionein-III (MT-III) is a brain-specific metallothionein, which is markedly reduced in the brain of patients with Alzheimer's disease (AD) and other degenerative diseases. Oxidative stress seems to be one of the principal factors that modulate MT-III mRNA (Messenger Ribonucleic Acid) expression. Pulmonary surfactant, a mixture of phospholipids and surfactant proteins (SP-A and SP-B) reduces surface tension at the air-liquid interface and protects the large epithelial surface of the lung from infectious organisms. Cellular oxidants reduce surfactant protein expression. Also, antioxidants reduce cyclooxygenase-2 expression, prostaglandin production and proliferation in colorectal cancer.

Overexpression of mdr-1 type transporters in tumor cells contributes to multidrug-resistance. The induction of mdr-1 mRNA and of functionally active mdr1-type P-glycoprotein by elevation in intracellular levels of reactive oxygen species and the repression of intrinsic mdr-1 mRNA and P-glycoprotein overexpression by antioxidants support the conclusion that the expression of the mdr-1b P-glycoprotein is regulated in a redox-sensitive manner.

Oxidative stress regulates the expression of various regulatory genes in rabbit lens epithelial cells, which likely affects cell proliferation, differentiation, and viability and thus affects normal cell function [CA 127:230414h].

In cultured keratinocytes, butylated hydroxytoluene hydroperoxide (BHTOOH) stimulates a time-dependent increase in ornithine decarboxylase (ODC) enzyme activity paralleled by induction of ODC mRNA (mRNA that directs ODC synthesis), suggesting transcription regulation of ODC by BHTOOH. Depletion of intracellular glutathione caused a 5-fold potentiation of keratinocyte sensitivity to BHTOOH and consequently, of tumor promotion.

ROI's can also act indirectly as signal transducers by modifying the bioavailability of nitric oxide (NO). Thus, inflammatory cytokines such as tumor necrosis factor-alpha (TNF-α) and interleukins (IL's) induce NO (nitric oxide) overproduction. NO is a messenger endogenously synthesized by a variety of mammalian cells including neurons, smooth muscle cells, macrophages, neutrophils, and platelets. In fact there is cross-talk between ROI's and NO, since the effects of the latter are influential on signaling pathways regulated by thiolic redox status.

However, if superoxide and NO interact a powerful non-radical oxidant, peroxynitrite (PN), is readily formed. PN is capable of oxidizing a number of biomolecules and complex cell structures including enzymes such as catalase and glutamine synthetase, proteins containing tyrosine residues, DNA, brain mitochondria and membrane lipids such as synaptosomal membranes.

NO itself has been implicated in a variety of neurodegenerative disorders and is a mediator in excitotoxic and post-hypoxic damage to neurons. DNA strand breakage is induced synergistically by NO and a catecholamine.

Most living organisms have evolved well-integrated antioxidant defense mechanisms, which include both antioxidant enzymes such as catalase, superoxide dismutases, glutathione peroxidases, quinone reductase, diaphorase and ceruloplasmin and low molecular weight antioxidants (LMWAO's) such as pyruvic acid, glutathione (GSH), dihydrolipoic acid (DHLA), beta-carotene, vitamin C, vitamin E and thioredoxin (TRX, a ubiquitous, relatively small, dithiolic, hydrogen-carrier protein).

Whereas antioxidant vitamins and beta-carotene must be supplied through food intake (e.g. in fruits and vegetables), both the thiolic tripeptide glutathione and DHLA are endogenous antioxidants, as well as pyruvic acid.

Pyruvic acid, being a normal tissue metabolite, is likely to be non-toxic and its high effectiveness as a "peroxide scavenger" is well documented; furthermore, after scavenging hydrogen peroxide or organic hydroperoxides it is converted into acetic acid, which means that it is intrinsically incapable of acting as a prooxidant. In spite of these attributes, pyruvic acid's role as an endogenous antioxidant has been widely underestimated: it is probably an important but underrated contributor to the "redox buffering" capacity of blood serum.

Glutathione (L-gamma-glutamyl-L-cysteinylglycine) is a ubiquitous intracellular thiol present in almost all mammalian tissues; the liver has very high intracellular levels of GSH.

Besides maintaining cellular integrity by enforcing a reducing environment, GSH has multiple functions including detoxification of xenobiotics; synthesis of proteins, nucleic acids, leukotrienes, prostaglandins and thromboxanes through its action as a coenzyme; and preventing other antioxidants from becoming pro-oxidants.

GSH enforces a reducing intracellular environment by acting as an excellent scavenger of both oxygen-centered and nitrogen-centered free radicals (reactive nitrogen intermediates, RNIs) and by readily converting non-radical oxidants (PN, peroxides, hydroperoxides) into harmless compounds. After acting as a coenzyme or scavenging ROI's or PN, GSH is oxidized to GSSG (glutathione disulfide), from which GSH is regenerated enzymatically. The redox system of GSH consists of primary and secondary antioxidants, including glutathione peroxidases, glutathione reductase, glutathione-S-transferase, and glucose-6-phosphate dehydrogenase.

Redox reactions in which GSH plays a role include protein folding, conversion of ribonucleotides to deoxyribonucleotides, and maintenance of reduced pools of vitamins C and E; GSH can also undergo reversible thiol-disulfide exchange with proteins containing oxidized cysteine (i.e., cystine) residues.

Whereas in tissues and red blood cells (CA 131:156247v) GSH is the foremost "redox buffer", in blood plasma this function has been assigned to albumin, although this applicant believes that pyruvic acid is also a key antioxidant in both environments.

As stated above, DHLA and thioredoxin perform roles that complement those of GSH; their oxidized forms can also be reduced easily by enzyme action. Vitamins C and E, which can readily and reversibly act as hydrogen donors as well, also contribute to maintain the intracellular oxidant-reductant balance (redox homeostasis).

By operating in a concerted and often synergistic manner, the redox mediators GSH, DHLA, TRX, Vitamin C, Vitamin E, and the antioxidant enzymes help maintain a reducing intracellular environment. This reducing environment performs a variety of important cellular functions. First, it helps keep bioactive quinones in the reduced state. For example, cardiotonic ubiquinones and vitamin K are maintained in their reduced state (ubiquinol/hydroquinone), so as to minimize the probability of arylating DNA and of generating ROI's in anaerobic or aerobic conditions. Also, it keeps catecholamines (adrenaline, dopamine, etc.) in the reduced (hydroquinone) condition, preventing their irreversible oxidation to quinoneimines of the adrenochrome type. The reducing intracellular environment also prevents vasoactive serotonin from being oxidized to a reactive quinoneimine.

The reducing intracellular environment prevents inactivation of heart dihydrolipoamide dehydrogenase and of other oxidant-sensitive enzymes such as glutamine synthetase. The reducing environment attenuates hypersensitivity responses induced by oxidative activation of phenolic haptens, and preserves the functional integrity of the blood-brain barrier, of the intestinal epithelium, and of the heart endothelium. It also helps preserve cytoskeletal integrity. The reducing environment protects synaptosomal membranes from oxidation, and prevents the death of hippocampal neurons. It is also important to phagocytes, as it supports their random migration, chemotaxis, ingestion and superoxide production.

Of particular significance is the role of a reducing environment in preserving the functional integrity of mitochondria. GSH and glutathione peroxidase (GPx) play a critical role here, since mitochondria lack catalase, an enzyme which degrades hydrogen peroxide. "Mitochondrial diseases" are disorders to which deficits in mitochondrial respiratory chain activity contribute. This category includes deficiencies in the activity of components of the mitochondrial respiratory chain. Typically, these deficiencies are caused by exposure of the cells to nitric oxide and hypoxia or ischemia or oxidative stress on the tissue. These deficiencies in antioxidants or antioxidant enzymes can result in or exacerbate mitochondrial degeneration. It must be pointed out that redox homeostasis also requires a delicate antioxidant enzyme balance in cells: too much Superoxide Dismutase (SOD) relative to GPx or catalase results in the accumulation of hydrogen peroxide, which in turn, through the Fenton reaction, leads to the production of hydroxyl radical and concomitant cell damage. However, too little SOD enzyme is also not favorable because superoxide radicals in themselves are toxic to cells. Therefore, fine-tuning of the antioxidant enzymes (together with the nonenzymatic antioxidants) becomes imperative if the cell is to function successfully in an oxygen-rich environment.

Down syndrome is believed to be the consequence of a congenital perturbation in the balance of antioxidant enzymes, with damage to important biomolecules brought about by a highly pro-oxidant intracellular environment.

In the face of stresses such as injury or infection, organisms rapidly marshal a host of responses: immune cells are recruited and various genes are rapidly activated. The key coordinating factor in this activation is the nuclear transcription factor NF-κB, which also plays a crucial role in modulating gene expression during growth and development.

Among the genes modulated by NF-κB are those encoding cytokines (TNF-α, IL's, etc.) and growth factors, immunoreceptors, adhesion molecules, acute-phase proteins, other transcription factors and regulators, NO-synthase, and viral genes. Most target genes for NF-κB are intrinsically linked to a coordinated inflammatory response.

NF-κB has far-reaching significance for a variety of pathological conditions in which inflammation, growth, or viral activation occur, such as tumor genesis, HIV infection (AIDS), atherosclerosis, diabetes, rheumatoid arthritis, chronic bronchitis, cystic fibrosis, idiopathic pulmonary fibrosis, ARDS, septic shock, cirrhosis, ulcerative colitis, reperfusion injury, inflammatory bowel disease, pulmonary emphysema, neurodegenerative disorders, (Alzheimer's Disease, Parkinson's Disease, etc.), osteoporosis, asthma, renal disease, rheumatoid synovitis, and the animal model of multiple sclerosis, experimental allergic encephalomyelitis.

An important NF-κB regulated gene is that encoding the cytokine TNFα which plays a central role in several inflammatory conditions. Since TNF-α is itself an activator of NF-κB, the potential for a positive inflammatory feedback cycle with disastrous consequences can be envisioned.

As stated above, the activation of NF-κB has been implicated in a wide range of diseases in which there is an inflammatory and/or hyperproliferative component including AIDS, where the expression of HIV is NF-κB dependent. It is now clear that ROI/RNI are mediators of NF-κB activation, and also that this process can be blocked by antioxidant agents.

Antioxidant agents can also inhibit the production of TNF-α. Excessive or unregulated TNF-α production mediates or exacerbates a number of diseases including rheumatoid arthritis, rheumatoid spondylitis, osteoarthritis, gouty arthritis, sepsis, septic shock, endotoxic shock, gram-negative sepsis, toxic shock syndrome, ARDS, cerebral malaria, chronic pulmonary inflammatory disease, silicosis, asbestosis, pulmonary sarcoidosis, bone resorption diseases, reperfusion injury, graft vs. host reaction, allograft rejections, cachexia secondary to infection or malignancy, cachexia secondary to acquired immune deficiency syndrome (AIDS), AIDS related complex, keloid formation, scar tissue formation, Crohn's disease, ulcerative colitis, pyrosis and fever and myalgias due to infection.

Although most experts would admit the possibility that "the time course and even the final outcome, of a disease can be critically modulated by strengthening the antioxidant side of the balance between prooxidants and antioxidants, it is unfortunately true that single antioxidants as pharmacologically active agents have not been found to exhibit extremely powerful therapeutic effects. For example, the jury is still out regarding the effectiveness of vitamin C as a therapeutic agent. Nevertheless, vitamin C may have a role in impeding the progress of diabetes, cataract, heart disease, cancer, aging, and a variety of other disease states. Several methods for modulating cellular GSH levels in human diseases associated with GSH deficiency and oxidative stress are still being evaluated. DHLA, regarded in some quarters as a unique "ideal" antioxidant remains an intriguing possibility for the treatment of conditions (notably AIDS, atherosclerosis and diabetes) related to oxidative stress.

Treatment of severe vitamin E deficiency with appropriate supplements of the vitamin can at least halt the progression of the characteristic neurological features, but in the majority of clinical neurological conditions the therapeutic benefits of antioxidant supplementation still requires to be proved. On the other hand, vitamin E has been reported to regress oral leukoplakia (a precancerous lesion). Supplemental beta-carotene reduces the frequency of "oral micronuclei" (an indicator of genotoxic damage to the oral epithelium) significantly; it is also effective against oral leukoplakia. Preliminary results of studies on pre-cachectic and cachectic HIV-infected patients indicate that the decrease of plasma cystine, glutamine, and arginine levels can be corrected by N-Acetyl-L-Cysteine (NAC). Anecdotal data also suggest that this strategy may slow or even prevent the progression of the disease.

A preliminary report indicates that ARDS patients receiving NAC (by mouth), alpha-tocopherol (by mouth), selenium (iv) and ascorbic acid (iv) within 24 hrs of diagnosis for 3 days experienced a significant reduction in mortality (n=25; 20% mortality) compared to a control group (n=20; 65% mortality); however, these results are in need of validation.

Finally, a randomized trial (n=65) with biopsy-confirmed transitional cell bladder carcinoma patients yielded promising results: the 5-year estimate of tumor recurrence was 91% in the "RDA arm" (patients receiving multivitamins at RDA (Recommended Daily Allowance) levels) vs. 41% in the "megadose arm" (patients receiving multivitamins at RDA levels plus 40,000 IU retinol plus 100 mg pyridoxine plus 2000 mg ascorbic acid plus 4000 IU alpha tocopherol plus 90 mg zinc).

This rather limited success might seem at first surprising in view of the decreased levels of selected major antioxidants consistently found in a number of disease states (GSH in AIDS, hepatitis C, type II diabetes, ulcerative colitis, A.R.D.S., idiopathic pulmonary fibrosis and neurodegenerative syndromes; vitamin E in atherosclerosis, ARDS, Down syndrome and Alzheimer's disease; ascorbic acid in ARDS; beta-carotene in cystic fibrosis; vitamin A in Down syndrome and Alzheimer's disease, etc.). On second thought, however, the limited success of this "magic single antioxidant approach" can be rationalized by recalling that mammals possess highly evolved and well-integrated antioxidant mechanisms which require the concerted and synergistic action of both antioxidant enzymes and low molecular weight antioxidants, with different antioxidants operating extracellularly and/or in specific cell compartments (aqueous vs. lipidic microenvironments) and having limited functional overlap. Some antioxidants destroy peroxidic species and/or PN, others break free radical chains, still others quench singlet oxygen.

There are other foreseeable obstacles in the way of the "single antioxidant" approach to therapy. Several antioxidants have been shown to be capable of acting as pro-oxidants or as NF-κB activators "in vitro" and/or "in vivo" under rather specific conditions, including ascorbic acid, beta carotene, glutathione, flavonoids, NAC, and L-cysteine. Limited evidence suggests that administration of a single antioxidant might have adverse effect(s) on plasma levels of other antioxidants.

After this appraisal of the current biochemical research on the etiology of cancer, AIDS, cardiovascular diseases, diabetes, Down syndrome, neurodegenerative disorders and chronic inflammatory diseases, the following hypotheses might help explain the remarkable success of the therapy system herein described:

The sulfur compounds comprised by the therapy system herein disclosed act as inducers of antioxidant enzymes, thereby enhancing the immune system and/or reactivating mitochondria and/or increasing GSH levels, i.e. their effects are similar to those of 1,2-dithiole-3-thiones. The sulfur compounds herein disclosed act as powerful antioxidant enzyme activators. Specifically, they interact chemically, as reductants, with inactivated enzymes containing disulfide bonds which are thereby cleaved and converted into thiol groups with concomitant restoration of enzyme function. In this case their effect would be akin to that of hydrogen sulfide on inactivated (oxidized) papain. The sulfur compounds on which the present invention is based act indirectly through the delivery of "reducing equivalents" to cells subject to oxidative stress, their effect being restoration of redox homeostasis and immune function. The mediator might well be pyruvic acid (see above) since it is known that pyruvic acid can act systemically when delivered to the gut; i.e. it can be readily transported from the gut to other tissues. Further, pyruvate has been shown to enhance the endogenous GSH system Also, there is a linear relationship between GSSG-to-GSH and lactate-to-pyruvate ratios in human blood before, during and after exercise.

In a study on the nutritional requirements of human gut sulfate-reducing bacteria, it was found that short-chain fatty acids such as butyric acid, lactic acid, and other organic acids; alcohols; and amino acids (but not sugars or aromatic compounds) stimulated sulfate reduction. Experiments with two strains of *Desulfovibrio desulfuricans* isolated from human feces demonstrated that both were able to reduce sulfite, thiosulfate or nitrate in the absence of sulfate.

Therefore, while the present invention is not to be restricted by any hypothesis, it is possible that pyruvate, synthesized in the gut by bacterial microflora from lactate and sulfite or thiosulfate (or some other sulfur species capable of undergoing reduction), is then transported to the mammal's tissues, wherein it acts, mainly at the mitochondrial level, as a peroxide scavenger and a source of both NADH and energy (via acetyl coenzyme A). NADH (reduced nicotinamide adenine dinucleotide) can then enzymatically reduce lipoic acid (LA) to DHLA, which can in turn reduce GSSG to GSH.

Considering the seriousness of the AIDS pandemic, the global burden of cancer (with close to 10 million newly diagnosed cases each year), and the devastating effects of such diseases as diabetes, chronic inflammatory diseases, neurodegenerative pathologies, and Down syndrome it is clear that a pressing need exists for effective treatments of pathological states related to oxidative stress and/or exacerbated or mediated by NF-κB/TNF-α, such as the ones referred to above. This becomes even more clear when we consider the fact that cardiovascular diseases (and atherosclerosis, which is believed to be their underlying primary cause) are the main cause of death in most developed countries.

SUMMARY OF THE INVENTION

This invention relates to a novel method useful for treating cancer, AIDS, ARC, cachexia secondary to AIDS, cachexia secondary to cancer, diabetes, Down syndrome, cardiovascular diseases, Hypercholesterolemia and neurodegenerative diseases. This novel method, useful for treating said disease conditions, comprises the delivery of therapeutically-effective amounts of the following compounds, either individually or intermixed: sulfide compounds, thiosulfate compounds, thionite compounds, sulfite compounds, and thionate compounds to the gut of a mammal in need thereof.

This invention further comprises treatment by parenteral administration of thiosulfate compounds and/or thionate compounds and/or thionite compounds and/or sulfite compounds and/or sulfide compounds to a patient (or non-human mammal) afflicted with cancer, AIDS, ARC, cachexia secondary to cancer, cachexia secondary to AIDS, diabetes, Down syndrome, cardiovascular disease or a neurodegenerative disease.

This invention further comprises treatment of a patient (or non-human mammal) afflicted with cancer, AIDS, ARC, cachexia secondary to cancer, cachexia secondary to AIDS, diabetes, Down syndrome, cardiovascular disease or a neurodegenerative disease by administration of therapeutically—effective amounts of a least one of the compounds herein disclosed by any means that produces contact of the active agent or agents with their site of action in the mammal's body.

This invention also relates to pharmaceutical compositions comprising one or more of the above-mentioned compounds, or pharmaceutically acceptable organic, inorganic or organometallic precursors thereof, and one or more pharmaceutically acceptable excipients, carriers, diluents or adjuvants.

This invention further relates to a method for preparing pharmaceutically acceptable dosage forms containing the aforementioned ingredients and capable of releasing the pharmacologically active ingredient or ingredients in the gut of a mammal in need thereof. This invention further comprises the novel preparation of active sulfur compounds for oral use, by combining the active ingredients with "enteric carriers" (defined as a carrier, mixed with the drug, that carries active drug to the gut). In the absence of an enteric carrier, the disclosed active compounds produce almost unbearable gastric distress upon reacting with acid in the stomach and concomitant release of large volumes of gaseous (and toxic) hydrogen sulfide. One novel enteric carrier is wet microcrystalline or powdered cellulose, which previously had been known as a disintegrant. Without wishing to be bound by theory, we believe that mixing highly reactive sulfides with wet cellulose (or other materials with the same characteristics) prevents the rapid release of the sulfides in the areas were they can produce damage as well as their almost instantaneous reaction with acid in the stomach with concomitant release of large volumes of gaseous hydrogen sulfide. Otherwise (as is usually the case ) when an ordinary gelatin capsule containing drug and MCC reaches the stomach and gastric juice—which contains mainly water—contacts the dry MCC, this highly porous material (by "wicking action") rapidly absorbs gastric juice, disintegrates (as intended) and the capsule's contents are quickly released in the stomach. The wet cellulose, in contrast, being already wet absorbs significantly less water, thus remaining intact until it reaches the gut.

The present invention also comprises the use of combination therapies involving administration of the aforementioned active ingredients.

The present invention further comprises administering one of the formulations herein described to non-human mammals, i.e. as veterinary medication for treatment of said non-human mammals in need thereof.

DESCRIPTION OF EMBODIMENTS OF THE INVENTION

Definitions: Sulfide compounds are compounds formally containing the divalent $S_n$ moiety (S=sulfur; n=1, 2, 3 . . . ) chemically bonded to hydrogen and/or a metal (or metals) and/or a polyatomic cation (or cations) such as hydrogen sulfide, hydrogen disulfide, hydrogen tetrasulfide, sodium hydrosulfide, sodium hydrosulfide dihydrate, sodium sulfide, sodium sulfide nonahydrate, potassium sulfide, calcium sulfide, iron(II) sulfide, silicon (IV) sulfide, zinc sulfide, bismuth (III) sulfide, sodium disulfide, magnesium disulfide, iron (II) disulfide, sodium tetrasulfide, barium tetrasulfide, potassium pentasulfide, cesium hexasulfide, potassium iron (III) sulfide, ammonium sulfide, ammonium disulfide, ammonium tetrasulfide, and the like.

Sulfite compounds are compounds formally containing the divalent sulfite moiety ($SO_3$) chemically bonded to hydrogen, and/or a metal (or metals) and/or a polyatomic cation (or cations), such as sodium sulfite, potassium sulfite, ammonium sulfite, calcium sulfite, cesium hydrogensulfite, and the like.

Thiosulfate compounds are compounds formally containing the divalent thiosulfate moiety ($S_2O_3$) chemically bonded to hydrogen and/or a metal (or metals) and/or a polyatomic cation (or cations), such as sodium thiosulfate ($Na_2S_2O_3$), potassium thiosulfate ($K_2S_2O_3$), sodium thiosulfate pentahydrate ($Na_2S_2O_3.5H_2O$), magnesium thiosulfate ($MgS_2O_3$), silver thiosulfate ($Ag_2S_2O_3$), ammonium thiosulfate [$(NH_4)_2S_2O_3$], and the like.

Thionate compounds are compounds formally containing the divalent $S_nO_6$ (n>1) moiety chemically bonded to hydrogen and/or a metal (or metals) and/or a polyatomic cation (or cations), such as calcium dithionate (CaS2O6), barium dithionate dihydrate (BaS2O6.2H2O), sodium trithionate, sodium tetrathionate and the like.

Thionite compounds are compounds formally containing the divalent SnO2n (n=1 or 2) moiety chemically bonded to a hydrogen and/or a metal (or metals) and/or a polyatomic cation (or cations) such as zinc sulfoxylate, zinc dithionite, sodium dithionite, sodium dithionite dihydrate, and the like.

Organic, inorganic or organometallic precursors of the previously defined compounds are any and all chemical species from which sulfide compounds and/or sulfite compounds and/or thiosulfate compounds and/or thionite compounds and/or thionate compounds, can arise through chemical change and/or enzyme action and/or biotransformation in a mammal's body. Therefore, tetraphosphorus decasulfide (P4S10), sodium thiosilicate (Na2SiS3) and elemental sulfur are precursors of sulfide compounds; whereas sodium metabisulfite (Na2S2O5), diethyl sulfite and sodium sulfate are precursors of sulfite compounds.

Active sulfur compounds, as defined in the current invention, encompass:

1) sulfide compounds, 2) sulfite compounds, 3) thiosulfate compounds, 4) thionate compounds, 5) thionite compounds, and 6) organic, inorganic or organometallic precursors of sulfide compounds, sulfite compounds, thiosulfate compounds, thionate compounds, and thionite compounds.

Treatment by delivery to the gut of a mammal of therapeutically effective amounts of the active ingredient(s) includes:

a) Administration of a solution or dispersion of the active ingredient(s) by enteroclysis.

b) Oral administration of enterically coated tablets, granules, capsules, etc. which contain the active ingredient(s) and (optionally) one or more carriers and/or diluents and/or adjuvants. The composition may be administered in the form of tablets coated with an enteric coating; capsules having a shell, a filling comprising the active ingredient, and an enteric coating on the shell; or enterically coated granules comprising the active sulfur compound. The enterically coated granules may be included within a tablet, or as a filling within a capsule.

c) Oral administration of non enterically-coated capsules containing the active ingredient(s) and (optionally) one or more carriers and/or diluents and/or adjuvants intimately admixed with, and/or absorbed into, and/or adsorbed onto, an enteric carrier, such as wet microcrystalline cellulose.

d) Oral administration of delayed-release formulations containing the active ingredient(s) and (optionally) one or more carriers, diluents and adjuvants.

e) Rectal administration, as by using suppositories containing the active ingredient(s) and (optionally) one or more carriers, diluents and adjuvants.

f) Coadministration of the active ingredient (s) with any other pharmacologically active agents such as vitamins, micronutrients, coenzyme Q10, glucosamine, chondroitin sulfate, triiodothyronine, vinpocetine, pramiracetam, piracetam, hydergine, choline, niar, gallic acid, diallyl sulfide, anti-cancer agent (s), immunostimulant (s), antibiotic(s), hormone antagonist (s), antiviral agent(s), antihypertension agent(s), insulin and anti-inflammatory agent (s), optionally including one or more vehicles, carriers, diluents and adjuvants either orally [as in b), c), or d) above] or by enteroclysis [as in a) above] or rectally [as in e) above].

Parenteral administration to a patient (or non-human mammal) includes:

a) Intravascular administration of solutions/dispersions containing at least one of the compounds herein disclosed and, optionally, other active agents and/or one or more adjuvants.

b) Intramuscular administration of solutions/dispersions containing at least one of the compounds herein disclosed and, optionally, other active agents and/or one or more adjuvants.

c) Subcutaneous administration of solutions/dispersions containing at least one of the compounds herein disclosed and, optionally, other active agents and/or one or more adjuvants.

d) Intrathecal administration of solutions/dispersions containing at least one of the compounds herein disclosed and, optionally, other active agents and/or one or more adjuvants.

e) Transdermal administration of appropriate formulations containing at least one of the compounds herein disclosed and, optionally, other active agents and/or one or more adjuvants.

f) Transmucosal administration of appropriate formulations containing at least one of the compounds herein disclosed and, optionally, other active agents and/or one or more adjuvants.

g) Sublingual administration of appropriate formulations containing at least one of the compounds herein disclosed and, optionally, other active agents and/or one or more adjuvants.

The term mammals is intended to mean both human and non-human mammals.

As used herein, therapeutically-effective amount refers to that amount that must be administered per day to a patient (on non-human mammal) in order to achieve an anti-tumor effect; to modulate an immune response; to modulate gene expression; to ameliorate Down syndrome; to treat hypercholesterolemia; to treat leukemia; to treat diabetes or to treat cardiovascular disease. Methods of determining therapeutically effective amounts are well known.

By disease-associated problem is meant a health problem derived from a specific disease, such as "cachexia secondary to cancer" or "muscle degeneration secondary to AIDS".

As used herein, gut means intestine.

As used herein, a pharmaceutically acceptable component is one that is suitable for use with humans and/or non-human mammals without undue adverse side effects (such as toxicity, irritation and allergic response) commensurate with a reasonable benefit/risk ratio.

By safe and effective amount is meant the quantity of a composition which is sufficient to elicit a desired therapeutic response without undue adverse side effects (such as toxicity, irritation or allergic response) commensurate with a reasonable benefit/risk ratio when used in the manner of this invention.

As used herein, combination therapy means that the patient (or non-human mammal) in need of treatment according to the present invention, is given medication not herein contemplated in addition to that herein disclosed. Combination therapy can be sequential therapy where the patient or non-human mammal is treated first with one or more drugs and then the other(s), or simultaneous therapy, when all drugs are co-administered.

As used herein "disease mediated by oxidative stress" means health conditions causally related to a failure of cells to maintain REDOX HOMEOSTASIS, which directly leads to oxidative damage by ROI's (Reactive Oxygen Intermediates) and RNI's (Reactive Nitrogen Intermediates). When the finely tuned balance between antioxidants and oxidants is tilted in favor of the latter, biomolecules, cell membranes and mitochondria are damaged, the immune system is compromised, cell-signaling and inflammation go awry and—since mitochondria regulate apoptosis—the outcome is usually either a degenerative disease (diabetes and its vascular complications, anemia, arthritis, Parkinson's Disease, Alzheimer's Disease, amyotrophic lateral sclerosis, Huntington's Disease, muscular dystrophy, myotonic dystrophy, chronic fatigue syndrome, Friedreich's ataxia, ocular lens opacification, nephrosis, liver necrosis, pulmonary immune deficits, hepatic encephalopathy, macular degeneration, age-associated memory impairment, Creutzfeldt-Jacob's Disease, stroke, epilepsy, peripheral neuropathy, optic neuropathy, anatomic neuropathy, neurogenic bowel disease, sensorineural deafness, neurogenic bladder dysfunction, migraine, renal tubular acidosis, dilating cardiomyopathy, hepatic failure, lactic acidemia, arsenic poisoning, silicosis, acetaminophen poisoning, asbestosis, asthma, rheumatic polyarthritis, adult respiratory distress syndrome, etc.) or a hyperproliferative disease such as cancer, AIDS, herpes simplex virus-1 infection, cytomegalovirus-induced vascular pathology, arteriosclerosis, ARC, hepatitis, trypanosomiasis, vascular restenosis, psoriasis, glomerular nephritis, transplant rejection, etc.

Mitochondrial diseases are disorders to which deficits in mitochondrial respiratory chain activity contribute. This category includes:

a) Congenital genetic deficiencies in activity of one or more components of the mitochondrial respiratory chain, and b) Acquired deficiencies in the activity of one or more components of the mitochondrial respiratory chain, wherein such deficiencies are caused by, inter alia, oxidative damage during aging, and/or exposure of affected cells to NO.

Finally, a number of abbreviations are used in this application. The abbreviation ASK, as used herein, relates to the protein apoptosis signal-regulating kinase. The abbreviation IU refers to International Unit. The abbreviation LTR relates to the phrase long terminal repeat, while mdr relates to multiple drug resistance.

The applicant has demonstrated that delivery to a patient (or non-human mammal) afflicted with cancer, hypercholesterolemia/cardiovascular disease, or Down syndrome of safe and effective amounts of the compositions herein disclosed constitutes an effective treatment method.

In cancer patients, treatment in accordance with this invention will usually bring about a rapid and marked reduction of tumor size: such size reduction is characteristic clinical evidence for malignant cell death and degeneration (oncolysis); a similar reduction in malignant cell content of tissues containing disperse (nonaggregated) malignant cells will also usually result from treatment carried out as prescribed in this invention. In fact, dosage should be closely monitored to avoid any side effects due to either medication toxicity or massive release of toxins by malignant cell's lysis; it may be preferable to treat in short courses of several days, leaving a few days in between.

In acute situations the patient or non-human mammal can be given a high initial "loading dose", followed by a 50% lower "maintenance dose".

In every instance close monitoring of the patient or non-human mammal is necessary, especially upon initial administration of any of the formulations herein disclosed, since a mild or severe allergic reaction (including anaphylactic shock) might ensue in susceptible individuals. Although such allergic reaction was not observed in any of the numerous patients treated thus far, it is a well-known fact that oral administration of sulfites and metabisulfites has provoked this kind of reaction (asthmatic episodes, for instance) in susceptible individuals.

Fortunately, sulfite susceptibility among the general population is probably very low, since "sulfite compounds" are widely used as "pharmaceutical aids" (antioxidants) in many types of dosage forms for oral administration ("The Merck Index" 12.sup.th Edition, monograph #8784, Merck and Co., 1996). However, it is also known that the prevalence of sulfite susceptibility among asthmatic patients is higher than among the general population; therefore it is advisable to ensure that patients in this "high risk" group be screened and declared not susceptible to orally-administered sulfites before treatment is instituted.

It will be envisaged by those skilled in the art that the actual daily dosages of the foregoing compositions to be administered to a patient or to a non-human mammal will lie entirely within the discretion of the physician or veterinarian, as the case might be. Thus, the daily dosage for an adult human male of average weight (i.e. about 70 Kg) should be greater than that for a child (or for a non-human mammal of lesser weight than the average human male) if other factors are equal, but the converse would be expected when dealing with e.g. either humans or non-human mammals heavier than the average human male.

Additionally, of course, the appropriate dosage administered in any given case will vary with the age, general health condition, nature and extent of symptoms and nature of concurrent treatment (if any).

In all cases, treatment must be adjusted as required on the basis of frequent individual clinical evaluations, with due consideration of appropriate test results.

The preferred dosage levels are about 1 capsule per 2 Kg of patient (or non-human mammal) weight per day for all the compositions herein disclosed but—as discussed above—should be adjusted on an individual basis, and may be increased by a factor of up to about 5 or decreased by a factor of up to about 10 if deemed necessary.

The invention can be illustrated by the following non-limitative examples.

FORMULATION EXAMPLE 1

Two hundred and fourteen (214) parts by weight sodium hydrogen sulfide (NaSH), six hundred and forty (640) parts by weight distilled water and two thousand (2000) parts by weight food grade microcrystalline cellulose were thoroughly blended at room temperature. The final powdery mixture was used for filling standard, two-piece hard gelatin capsules with 1,000 milligrams per capsule.

FORMULATION EXAMPLE 2

Three hundred and seventy two (372) parts by weight sodium thiosulfate (Na2S2O3), six hundred and forty (640) parts by weight distilled water and two thousand (2000) parts by weight food grade microcrystalline cellulose were thoroughly blended at room temperature. The resulting powdery mixture was used for filling standard two-piece hard gelatin capsules with 1,000 mg per capsule.

FORMULATION EXAMPLE 3

Four hundred and sixty four (464) parts by weight potassium metabisulfite (K2S2O5), six hundred and forty (640) parts by weight distilled water and 2,000 parts by weight food grade microcrystalline cellulose were thoroughly blended at room temperature. The resulting powdery mixture was used for filling standard, two-piece hard gelatin capsules with 1,000 mg per capsule.

FORMULATION EXAMPLE 4

One-thousand five-hundred and thirty-two (1532) parts by weight sodium thiosulfate (Na2S2O3), two-hundred and thirty-two (232) parts by weight potassium metabisulfite, two-hundred and twelve (212) parts by weight sodium metabisulfite, four hundred and eighteen (418) parts by weight sodium sulfide nonahydrate one thousand and ninety (1090) parts by weight distilled water and two thousand (2000) parts by weight food-grade microcrystalline cellulose were thoroughly blended at room temperature. The resulting powdery mixture was used for filling standard, two-piece hard gelatin capsules with 1,000 milligrams per capsule.

UTILITY EXAMPLE 1

Patient: Male, 74 year-old.

Baseline condition: Scarcely differentiated epidermoid larynx carcinoma associated with severe necrosis. The tumor is not operable on account of patient's marked cachexia and critical cardiovascular condition. Patient's status diagnosed as terminal.

Treatment regime: Administration of 24 capsules per day, each containing 1000 mg. of a formulation prepared as in "formulation example 1 " (approximately 75 mg. of active ingredient and 925 mg of inert ingredients).

Treatment outcome: At the end of the first week, tumor size was halved; at the end of the third week, tumor size was one fourth of original size.

UTILITY EXAMPLE 2

Patient: Male, 15 year-old.

Baseline condition: Acute lymphocytic leukemia refractory to conventional chemotherapy. Patient's status diagnosed as terminal.

Treatment regime: Administration of 18 capsules per day, each containing 1000 mg of a mixture prepared as in "formulation example 2" (approximately 125 mg of active ingredient and 875 mg of inert ingredients).

Treatment outcome: At the end of the second week, patient's blood count (leucocytes, erythrocytes and platelets) presented an alarming reduction, associated with a critical condition that required several blood transfusions.

At the end of the third week patient's condition was stable, presenting a normal blood count and a reduction in blast count from 90% to 38%.

At the end of the fourth week, all blood parameters were normal (including a zero blast count). Patient's status diagnosed as normal with total remission.

UTILITY EXAMPLE 3

Patient: Male, 38 year-old.

Baseline condition: Seminoma refractory to radiotherapy and to conventional chemotherapy.

Treatment regime: Administration of 30 capsules per day, each containing 1000 mg of the mixture prepared as in "formulation example 3" (approximately 150 mg of active ingredient and 850 mg of inert ingredients).

Treatment outcome: At the end of the first week, the persistent pain in the remaining testicle disappeared and the consistency of the testicle was almost normal.

At the end of the sixth month patient's status was diagnosed as normal with total remission.

UTILITY EXAMPLE 4

Patient: Male, 63 year-old.

Baseline condition: Colon carcinoma. The tumor's size precludes surgery. Patient's status diagnosed as terminal.

Treatment regime: Administration of 24 capsules per day, each containing 1000 mg of a formulation prepared as in "formulation example 4" (approximately 280 mg of sodium thiosulfate, 42 mg of potassium metabisulfite, 39 mg of sodium metabisulfite, 76 mg of sodium sulfide nonahydrate and 563 mg of inert ingredients).

Treatment outcome: At the end of the second month, the tumor had disappeared. Patient's status was diagnosed as normal with total remission.

Patient is still in good health 6 months after remission.

UTILITY EXAMPLE 5

Patient: Male, 15 year-old

Baseline condition: Testis carcinoma with bone (spine) metastasis. Patient's status diagnosed as terminal.

Treatment regime: Administration of 18 capsules per day, each containing 1000 mg of a formulation prepared as in "formulation example 4" (approximately 280 mg of sodium thiosulfate, 42 mg of potassium metabisulfite, 39 mg of sodium metabisulfite, 76 mg of sodium sulfide nonahydrate and 563 mg of inert ingredients).

Treatment outcome: At the end of the second week all subjective symptoms (pain, chronic fatigue, etc.) had disappeared.

At the end of the sixth week the spine tumor had disappeared.

Patient decided (on his own) to discontinue treatment and did so during the seventh, eighth, and ninth weeks. At the end of the ninth week, alarming symptoms forced the patient to seek help again: a CAT-scan showed the presence of two new tumors (one on a different spine location and the other in the previously unaffected testis) and the treatment was reinstituted with marked abatement of subjective cancer symptoms. When patient was confronted with the need to surgically ablate the previously unaffected testis, he refused and again discontinued treatment. Patient died two weeks after discontinuing treatment.

UTILITY EXAMPLE 6

Patient: Male, 4 year-old.

Baseline condition: Rhabdomyosarcoma of the nasopharynx, phase 4, refractory to radiotherapy and conventional chemotherapy. Patient's status diagnosed as terminal.

Treatment regime: 10 capsules per day, each containing 1000 mg of a formulation prepared as in "formulation example 4".

Treatment outcome: At the end of the second week a CAT-scan showed a halving in tumor size. At the end of the first month, a CAT-scan showed a 75% decrease in tumor size. At the end of the second month, a CAT-scan showed an 85% decrease in tumor size.

Patient is now asymptomatic.

UTILITY EXAMPLE 7

Patient: Male, 68 year-old.

Baseline condition: Lung carcinoma (phase 4) with bone (clavicle) metastasis, refractory to conventional chemotherapy. Patient's status diagnosed as terminal, with a life expectancy of at best two weeks.

Treatment regime: 16 capsules per day, each containing 1000 mg of a formulation prepared as in "formulation example 4".

Treatment outcome: At the end of the 12th week, a CAT-scan showed no tumor growth. Since then, the patient has been asymptomatic for 5 months.

UTILITY EXAMPLE 8

Patient: Female, 44 year-old.

Baseline condition: Breast adenocarcinoma, metastasized to bone and lymph nodes with the patient refusing to submit to either surgery or conventional chemotherapy.

Treatment regime: 20 capsules per day, each containing 1000 mg of a formulation prepared as in "formulation example 4".

Treatment outcome: At the end of the second week, a CAT-scan showed a 50% reduction in tumor size. At the end of the first month, a CAT-scan showed a 90% reduction in tumor size. At the end of the second month, patient status was diagnosed as normal with complete cancer remission.

UTILITY EXAMPLE 9

Patient: Female, 55 year-old

Baseline condition: Uterine corpus carcinoma, phase 4. Patient's status diagnosed as terminal.

Treatment regime: 40 capsules per day, each containing 1000 mg of a formulation prepared as in "formulation example 4".

Treatment outcome: At the end of the third month, patient status was diagnosed as normal with complete cancer remission.

UTILITY EXAMPLE 10

Patient: Male, 75 year-old

Baseline condition: Prostatic adenocarcinoma.

Treatment regime: 20 capsules per day, each containing 1000 mg of a formulation prepared as in "formulation example 4".

Treatment outcome: At the end of the sixth week, patient status was diagnosed as normal with complete cancer remission.

UTILITY EXAMPLE 11

Patient: Female, 26 year-old.

Baseline condition: Gluteal cancer, phase 4, refractory to radiotherapy and to conventional chemotherapy. Patient's status was diagnosed as terminal after five unsuccessful attempts at tumor removal by surgery. Patient complained of continuous excruciating pain, not amenable to treatment with analgesics.

Treatment regime: 18 capsules per day, each containing 1000 mg of a formulation prepared as in "formulation example 4".

Treatment outcome: At the end of the third day the excruciating pain subsided, leaving behind a sensation of discomfort. At the end of the first week, both the pain and the discomfort had disappeared completely. At the end of the 6th week there was evidence of massive tumor necrosis and concomitant reduction in tumor size.

UTILITY EXAMPLE 12

Patient: Female, 49 year-old.

Baseline condition: Leg liposarcoma, still present after several unsuccessful attempts at tumor removal by surgery.

Treatment regime: 20 capsules per day, each containing 1000 mg of a formulation prepared as in "formulation example 4".

Treatment outcome: At the end of the sixth month, patient status was diagnosed as normal with complete cancer remission.

UTILITY EXAMPLE 13

Patient: Male, 42 year-old

Baseline condition: Adenocarcinoma of the pancreas, phase 4. Patient status diagnosed as terminal.

Treatment regime: 25 capsules per day, each containing 1000 mg of a formulation prepared as in "formulation example 4.

Treatment outcome: At the end of the second month, patient status was diagnosed as normal with complete cancer remission.

UTILITY EXAMPLE 14

Patient: Female, 34 year-old

Baseline condition: Multiple myeloma.

Treatment regime: 18 capsules per day, each containing 1000 mg of a formulation prepared as in "formulation example 4".

Treatment outcome: At the end of the second month, complete remission was observed.

UTILITY EXAMPLE 15

Patient: Male, 58 year-old

Baseline condition: Hypercholesterolemia (total serum cholesterol 900 mg/dL).

Treatment regime: Administration of 20 capsules per day, each containing 1000 mg of a mixture prepared as in "formulation example 4"

Treatment outcome: At the end of the sixth week total blood cholesterol level was 200 mg/dL

UTILITY EXAMPLE 16

Patient: Male, 63 year-old

Baseline condition: Hypercholesterolemia (total serum cholesterol 700 mg/dL).

Treatment regime: Administration of 20 capsules per day, each containing 1000 mg of a mixture prepared as in "formulation example 4"

Treatment outcome: At the end of the sixth week, total blood cholesterol level was 248 mg/dL.

UTILITY EXAMPLE 17

Patient: Male, 74 year-old

Baseline condition: Hypercholesterolemia (total serum cholesterol 490 mg/dL).

Treatment regime: Administration of 20 capsules per day, each containing 1000 mg of a mixture prepared as in "formulation example 4"

Treatment outcome: At the end of the sixth week, total blood cholesterol level was 215 mg/dL.

UTILITY EXAMPLE 18

Patient: Male, 76 year-old
Baseline condition: Hypercholesterolemia (total serum cholesterol 618 mg/dL).
Treatment regime: Administration of 20 capsules per day, each containing 1000 mg of a mixture prepared as in "formulation example 4"
Treatment outcome: At the end of the sixth week, total blood cholesterol level was 195 mg/dL.

UTILITY EXAMPLE 19

Patient: Female, 56 year-old
Baseline condition: Hypercholesterolemia (total serum cholesterol 514 mg/dL).
Treatment regime: Administration of 20 capsules per day, each containing 1000 mg of a mixture prepared as in "formulation example 4"
Treatment outcome: At the end of the sixth week, total blood cholesterol level was 202 mg/dL.

UTILITY EXAMPLE 20

Patient: Male, 50 year-old
Baseline condition: Hypercholesterolemia (total serum cholesterol 883 mg/dL).
Treatment regime: Administration of 20 capsules per day, each containing 1000 mg of a mixture prepared as in "formulation example 4"
Treatment outcome: At the end of the sixth week, total blood cholesterol level was 206 mg/dL.

UTILITY EXAMPLE 21

Patient: Female, 58 year-old
Baseline condition: Hypercholesterolemia (total serum cholesterol 300 mg/dL).
Treatment regime: Administration of 20 capsules per day, each containing 1000 mg of a mixture prepared as in "formulation example 4"
Treatment outcome: At the end of the sixth week, total blood cholesterol level was 200 mg/dL.

UTILITY EXAMPLE 22

Patient: Male, 63 year-old
Baseline condition: Hypercholesterolemia (total serum cholesterol 472 mg/dL).
Treatment regime: Administration of 20 capsules per day, each containing 1000 mg of a mixture prepared as in "formulation example 4"
Treatment outcome: At the end of the sixth week, total blood cholesterol level was 218 mg/dL.

UTILITY EXAMPLE 23

Patient: Female, 3 year-old
Baseline condition: Down syndrome with severe mental retardation Treatment regime: Administration of 10 capsules per day, each containing 1000 mg of a mixture prepared as in "formulation example 4"
Treatment outcome: At the end of the tenth day, cognitive ability had improved significantly as evidenced by an increased attention span, and development of verbal skills. Additionally there were improvements in sphincter control and muscle tone. At the end of the sixth month, cognitive development had reached a level similar to that of a normal 2 year old girl.

UTILITY EXAMPLE 24

Patient: Female, 3 year-old
Baseline condition: Down syndrome with severe mental retardation and joint hyperflexibility.
Treatment regime: Administration of 10 capsules per day, each containing 1000 mg of a mixture prepared as in "formulation example 4" plus glucosamine sulfate (oral, 1500 milligrams per day), plus chondroitin sulfate (oral, 1200 milligrams per day).
Treatment outcome: At the end of the 14th day, cognitive ability had improved significantly as evidenced by an increased attention span and development of verbal skills. Additionally there were improvements in sphincter control and muscle tone. At the end of the sixth month, cognitive development had reached a level similar to that of a normal 2 year old girl. Additionally, a reduction in joint hyperflexibility was observed.

UTILITY EXAMPLE 25

Patient: Female, 3 year-old
Baseline condition: Down syndrome with severe mental retardation
Treatment regime: Administration of 10 capsules per day, each containing 1000 mg of a mixture prepared as in "formulation example 4" plus coenzyme Q10 (oral, 300 milligrams per day).
Treatment outcome: At the end of the tenth day, cognitive ability had improved significantly as evidenced by an increased attention span and development of verbal skills. Additionally there were improvements in sphincter control and muscle tone. At the end of the fifth month, cognitive development had reached a level similar to that of a normal two-and-a-half year old girl.

UTILITY EXAMPLE 26

Patient: Female, 4 year-old
Baseline condition: Down syndrome with severe mental retardation
Treatment regime: Administration of 10 capsules per day, each containing 1000 mg of a mixture prepared as in "formulation example 4"
Treatment outcome: At the end of the 10th day, cognitive ability had improved significantly as evidenced by an increased attention span and development of verbal skills. Additionally there were improvements in sphincter control and muscle tone. At the end of the twelfth month, cognitive development had reached a level similar to that of a normal 4 year old girl.

UTILITY EXAMPLE 27

Patient: Female, 4 year-old
Baseline condition: Down syndrome with severe mental retardation
Treatment regime: Administration of 10 capsules per day, each containing 1000 mg of a mixture prepared as in "formulation example 4" plus multivitamins
Treatment outcome: At the end of the 10th day, cognitive ability had improved significantly as evidenced by an increased attention span and development of verbal skills.

Additionally there were improvements in sphincter control and muscle tone. At the end of the tenth month, cognitive development had reached a level similar to that of a normal 4 year old girl.

UTILITY EXAMPLE 28

Patient: Female, 4 year-old
Baseline condition: Down syndrome with severe mental retardation
Treatment regime: Administration of 10 capsules per day, each containing 1000 mg of a mixture prepared as in "formulation example 4" plus choline (oral, 1000 milligrams per day) plus piracetam (oral, 1000 milligrams per day) plus pramiracetam (oral, 600 milligrams per day) plus selegiline (oral, 1 milligram per day), plus vinpocetine (oral, 5 milligrams per day), plus hydergine (oral, 5 milligrams per day)
Treatment outcome: At the end of the 10th day, cognitive ability had improved significantly as evidenced by an increased attention span and development of verbal skills. Additionally there were improvements in sphincter control and muscle tone. At the end of the seventh month, cognitive development had reached a level similar to that of a normal 4 year old girl.

UTILITY EXAMPLE 29

Patient: Female, 4 year-old
Baseline condition: Down syndrome with severe mental retardation and hypothyroidism.
Treatment regime: Administration of 10 capsules per day, each containing 1000 mg of a mixture prepared as in "formulation example 4" plus triiodothyronine (oral, 10 mcg per day).
Treatment outcome: At the end of the 10th day, cognitive ability had improved significantly as evidenced by an increased attention span and development of verbal skills. Additionally there were improvements in sphincter control and muscle tone. At the end of the eleventh month, cognitive development had reached a level similar to that of a normal 4 year old girl.

UTILITY EXAMPLE 30

Patient: Female, 4 year-old
Baseline condition: Down syndrome with severe mental retardation Treatment regime: Administration of 10 capsules per day, each containing 1000 mg of a mixture prepared as in "formulation example 4" plus triiodothyronine (oral, 10 mcg per day).
Treatment outcome: At the end of the 10th day, cognitive ability had improved significantly as evidenced by an increased attention span and development of verbal skills. Additionally there were improvements in sphincter control and muscle tone. At the end of the tenth month, cognitive development had reached a level similar to that of a normal 4 year old girl.

UTILITY EXAMPLE 31

Patient: Female, 4 year-old
Baseline condition: Down syndrome with severe mental retardation
Treatment regime: Administration of 10 capsules per day, each containing 1000 mg of a mixture prepared as in "formulation example 4" plus coenzyme Q10 (oral, 300 milligrams per day) plus triiodothyronine (oral, 10 mcg per day) plus choline (oral, 1000 milligrams per day) plus piracetam (oral, 1000 milligrams per day) plus pramiracetam (oral, 600 milligrams per day) plus niar (oral, 1 milligrams per day) plus hydergine (oral, 5 milligrams per day) plus vinpocetine (oral, 5 milligrams per day)
Treatment outcome: At the end of the 10th day, cognitive ability had improved significantly as evidenced by an increased attention span and development of verbal skills. Additionally there were improvements in sphincter control and muscle tone. At the end of the fifth month, cognitive development had reached a level similar to that of a normal 4 year old girl.

UTILITY EXAMPLE 32

Patient: Male, 68 year-old
Baseline condition: Patient confined to bed after several episodes of acute myocardial infarction. Patient status diagnosed as terminal.
Treatment regime: Administration of 20 capsules per day, each containing 1000 mg of a mixture prepared as in "formulation example 4" plus coenzyme Q10 (oral, 1000 milligrams per day).
Treatment outcome: At the end of the third month patient blood pressure was normal and he was able to walk and exercise moderately.

While the invention has been described in connection with specific embodiments thereof, it will be understood that it is capable of further modification and that this patent application is intended to cover any variations, uses or adaptations following, in general, the principles of the invention and including such departures from the present disclosure as come within the ordinary skill of the art to which the invention pertains, and as may be applied to the essential features hereinbefore set forth, within the spirit of the invention.

What is claimed is:

1. A pharmaceutical composition for treatment of a disease mediated by oxidative stress comprising:
    an active sulfur compound selected from sulfides, thionites, and thionates, or hydrates, and mixtures thereof, and
    an enteric carrier, wherein said sulfur compound is intimately admixed with or absorbed into or adsorbed onto said enteric carrier and said enteric carrier is present in an amount sufficient to deliver said active sulfur compound to the gut.

2. The pharmaceutical composition of claim 1 wherein said enteric carrier comprises cellulose and water.

3. The pharmaceutical composition of claim 1 wherein said enteric carrier comprises microcrystalline cellulose and water.

4. The pharmaceutical composition of claim 1, wherein said enteric carrier comprises powdered cellulose and water.

5. The pharmaceutical composition of claim 1 wherein said active sulfur compound is selected from the group consisting of hydrogen sulfide, sodium sulfide, sodium hydrogen sulfide, potassium sulfide, calcium sulfide, sodium hydrosulfide dihydrate, ammonium sulfide, sodium sulfide nonahydrate and combinations thereof.

6. The pharmaceutical composition of claim 1 wherein said pharmaceutical composition is about 7.50 parts sodium hydrogen sulfide, about 70.08 parts microcrystalline cellulose and about 22.42 parts water by weight.

7. The pharmaceutical composition of claim 1 wherein said pharmaceutical composition further comprises a pharmaceutically-acceptable non enteric excipient.

8. The pharmaceutical composition of claim 1 wherein said pharmaceutical composition is about 35.55 parts active sulfur compounds, about 36.47 parts microcrystalline cellulose, about 8.1 parts non-enteric excipient and about 19.88 parts water by weight, wherein said active sulfur compounds are selected from the group consisting of sodium sulfide nonahydrate, sodium hydrogen sulfide, and combinations thereof.

9. The pharmaceutical composition of claim 1 in the form of a granule, capsule, caplet or tablet.

10. A pharmaceutical composition for treatment of a disease mediated by oxidative stress comprising:
    an active sulfur compound selected from sulfides, thionites, thionates, hydrates, and mixtures thereof, wherein said active sulfur compound is intimately admixed with and absorbed or adsorbed onto a wet enteric microcrystalline cellulose carrier capable of delivering said active sulfur compound to the gut.

11. The pharmaceutical composition of claim 10 wherein said active sulfur compound is selected from the group consisting of sodium hydrogen sulfide, sodium sulfide nonahydrate, and combinations thereof.

12. The pharmaceutical composition of claim 10 wherein said pharmaceutical composition further comprises a pharmaceutically-acceptable non-enteric excipient.

13. The pharmaceutical composition of claim 10 in the form of a granule, capsule, caplet or tablet.

* * * * *